US008920836B2

(12) United States Patent
Hayes et al.

(10) Patent No.: US 8,920,836 B2
(45) Date of Patent: Dec. 30, 2014

(54) PARTICULATES

(75) Inventors: Geoffrey Gerard Hayes, Saffron Walden (GB); Hassan Mohammad, Ely (GB); Harjit Tamber, Hitchin (GB); Malcolm Walden, Hardwick (GB); Steve Whitelock, Milton (GB); Helen Kathleen Danagher, Cambridge (GB); Derek Allan Prater, Milton (GB)

(73) Assignee: Euro-Celtique S.A., Luxembourg (LU)

( * ) Notice: Subject to any disclaimer, the term of this patent is extended or adjusted under 35 U.S.C. 154(b) by 962 days.

(21) Appl. No.: 10/588,978

(22) PCT Filed: Feb. 11, 2005

(86) PCT No.: PCT/GB2005/050014
§ 371 (c)(1),
(2), (4) Date: Apr. 24, 2007

(87) PCT Pub. No.: WO2005/079760
PCT Pub. Date: Sep. 1, 2005

(65) Prior Publication Data
US 2007/0298103 A1 Dec. 27, 2007

(30) Foreign Application Priority Data

Feb. 12, 2004 (GB) .................................. 0403100.1
Jan. 28, 2005 (GB) .................................. 0501638.1

(51) Int. Cl.
A61K 9/22 (2006.01)
A61K 9/16 (2006.01)
(52) U.S. Cl.
CPC .................................. *A61K 9/1635* (2013.01)
USPC .......................................... 424/468; 514/282
(58) Field of Classification Search
None
See application file for complete search history.

(56) References Cited

U.S. PATENT DOCUMENTS

| | | | |
|---|---|---|---|
| 4,080,134 A | 3/1978 | Klaeysen et al. | |
| 4,242,219 A | 12/1980 | Bogerman et al. | |
| 4,801,460 A | 1/1989 | Goertz et al. | |
| 5,085,815 A | 2/1992 | Yeh et al. | |
| 5,290,560 A | 3/1994 | Autant et al. | |
| 5,552,159 A | 9/1996 | Mueller et al. | |
| 5,762,975 A | 6/1998 | Rockstedt | |
| 5,958,452 A * | 9/1999 | Oshlack et al. ............... | 424/457 |
| 5,965,161 A | 10/1999 | Oshlack et al. | |
| 6,290,990 B1 | 9/2001 | Grabowski et al. | |
| 6,509,038 B2 | 1/2003 | Baert et al. | |
| 7,572,463 B2 | 8/2009 | Bartholomaeus et al. | |
| 7,691,430 B2 | 4/2010 | Marsland | |
| 2001/0007678 A1 | 7/2001 | Baert et al. | |
| 2001/0018063 A1 | 8/2001 | Cummings et al. | |
| 2001/0033865 A1 | 10/2001 | Oshlack et al. | |
| 2001/0038852 A1 | 11/2001 | Kolter et al. | |
| 2002/0010127 A1 * | 1/2002 | Oshlack et al. ............... | 514/2 |
| 2003/0026839 A1 | 2/2003 | Oshlack et al. | |
| 2003/0044458 A1 * | 3/2003 | Wright et al. ............... | 424/458 |
| 2004/0170680 A1 | 9/2004 | Oshlack et al. | |
| 2006/0165790 A1 | 7/2006 | Walden et al. | |
| 2007/0259045 A1 | 11/2007 | Mannion et al. | |
| 2009/0029170 A1 | 1/2009 | Hayes et al. | |
| 2009/0148517 A1 | 6/2009 | Oshlack et al. | |
| 2010/0172974 A1 | 7/2010 | Oshlack et al. | |
| 2011/0104214 A1 | 5/2011 | Oshlack et al. | |
| 2012/0141583 A1 | 6/2012 | Mannion et al. | |

FOREIGN PATENT DOCUMENTS

| | | |
|---|---|---|
| EP | 0 465 338 A1 | 1/1992 |
| EP | 0 665 010 A1 | 8/1995 |
| EP | 1348429 | 10/2003 |
| EP | 1 889 621 A1 | 2/2008 |
| JP | 3-76721 A | 4/1991 |
| SE | 20020058677 A1 | 8/2002 |
| WO | WO 88/03795 A1 | 6/1988 |
| WO | WO 92/10173 A1 | 6/1992 |
| WO | 93/10765 | 6/1993 |
| WO | 96/14058 | 5/1996 |
| WO | WO 98/18610 A1 | 5/1998 |
| WO | WO 00/13687 A2 | 3/2000 |
| WO | 01/15667 | 3/2001 |
| WO | WO 01/58447 A1 | 8/2001 |
| WO | 02/05867 | 1/2002 |
| WO | 02/058677 A1 | 8/2002 |
| WO | 02/087512 | 11/2002 |
| WO | 03/004009 | 1/2003 |
| WO | 03/013433 | 2/2003 |
| WO | WO 03/084504 A2 | 10/2003 |
| WO | 2005/000310 | 1/2005 |
| WO | WO 2005/000310 A1 | 1/2005 |
| WO | WO 2005079760 A1 | 9/2005 |

OTHER PUBLICATIONS

Sood et al., Pharmaceutical Technology (Apr. 2004) pp. 62-85.
Amighi, K et al., "Evaluation of thermal and film forming properties of acrylic aqueous polymer dispersion blends: Application to the formulation of sustained-release film coated theophylline pellets" *Drug Development and Industrial Pharmacy* 21(20): 2355-2369 (1995).

(Continued)

*Primary Examiner* — Carlos Azpuru
*Assistant Examiner* — David Browe
(74) *Attorney, Agent, or Firm* — Sterne, Kessler, Goldstein & Fox P.L.L.C.

(57) ABSTRACT

A neutral poly(ethyl acrylate, methyl methacrylate) copolymer is employed as a carrier in the manufacture of pharmaceutical formulations containing an active ingredient. The formulations are preferably made by melt extrusion, and can have rubbery characteristics and can exhibit tamper resistance.

56 Claims, 5 Drawing Sheets

(56) References Cited

OTHER PUBLICATIONS

Bauer, K et al."Coated Pharmaceutical Dosage Forms: Fundamentals, Manufacturing Techniques, Biopharmaceutical Aspects, Test Mocthods and Raw Materials" Stuttgart: CRC Press (1998).
Degussa website/Pharma Polymers, "Pharmacopoeial Monographs and Drug Master Files" (Jun. 2004).
Degussa website/Pharma Polymers, "Products & Services" (Jan. 2005).
Degussa website, "Ibuprofene Sustained Release Matrix Tablets: Application of EUDRAGIT® NE 30 D" (Feb. 2002).
EVONIK Industries website: "Specifications and test methods for EUDRAGIT® NE 30 D" (Sep. 2007).
EVONIK Industries website: "Specifications and test methods for EUDRAGIT® NE 40 D" (Nov. 2007).
EVONIK Industries website: "Specifications and test methods for EUDRAGIT® NM 30 D" (Nov. 2007).
BASF website: "Kollidon® SR Technical Information" (Jul. 2007).
Wurster, DE et al., "Effect of curing on water diffusivities in acrylate free films as measured via a sorption technique" *AAPS PharmSciTech* 8(3): E1 (Article 71) (2007).
English language Abstract of Japanese Patent Publication No. JP 03-076721 A, Japanese Patent Office, PAJ, Japan (Dec. 2010).
European Search Report for European Patent Application No. EP 05 07 5341, European Patent Office, Rijswijk, Netherlands, mailed on Mar. 3, 2011.
International Search Report for International Application No. PCT/GB2005/050014, European Patent Office, Netherlands, mailed Aug. 4, 2005.
International Preliminary Report on Patentability for International Application No. PCT/GB2005/050014, European Patent Office, Netherlands, issued Aug. 14, 2006.
Office Action mailed Apr. 22, 2010, in U.S. Appl. No. 12/241,650, Hayes, G.G. et al., filed Sep. 20, 2008.
Office Action mailed Jan. 5, 2011, in U.S. Appl. No. 12/241,650, Hayes, G.G. et al., filed Sep. 30, 2008.
Office Action mailed Jun. 9, 2011, in U.S. Appl. No. 12/241,650, Hayes, G.G. et al., filed Sep. 30, 2008.
Office Action mailed Apr. 5, 2012, in U.S. Appl. No. 12/241,650, Hayes, G.G. et al., filed Sep. 30, 2008.
Office Action mailed Oct. 22, 2012, in U.S. Appl. No. 12/241,650, Hayes, G.G. et al., filed Sep. 30, 2008.
Office Action mailed May 22, 2013, in U.S. Appl. No. 12/241,650, Hayes, G.G. et al., filed Sep. 30, 2008.
Advisory Action mailed Apr. 3, 2013, in U.S. Appl. No. 12/241,650, Hayes, G.G. et al., filed Sep. 30, 2008.
Advisory Action mailed Mar. 22, 2011, in U.S. Appl. No. 12/241,650, Hayes, G.G. et al., filed Sep. 30, 2008.
Office Action mailed Mar. 31, 2008, in U.S. Appl. No. 11/056,035, Hayes, G.G. et al., filed Feb. 11, 2005.
Office Action mailed Mar. 14, 2014, in U.S. Appl. No. 12/241,650, Hayes, G.G. et al., filed Sep. 30, 2008.

\* cited by examiner

PARTICULATES

The present invention relates to particulates, and in particular to melt extruded multiparticulates which provide controlled release of an active ingredient.

BACKGROUND OF THE INVENTION

Multiparticulates of uniform dimensions with modified drug release properties can readily be manufactured by melt extrusion technology. Melt extrusion is a solvent-free single-step process for manufacturing multiparticulates and is particularly useful for drug release modification. By selection of suitable thermoplastic polymers and additives, melt extrusion technology can be used both to enhance the solubility, and subsequently the bioavailability, of poorly water soluble drugs as well as to retard drug release of moderate to highly water soluble drugs for controlled release products.

The backbone of melt extrusion technology is the application of thermoplastic materials which act as binders for embedded drugs in solution or dispersion form within the matrix. Thermoplastic polymers with low glass transition temperatures (Tg) are preferred for processing by melt extrusion. Lower processing temperatures are also preferred with respect to the stability of heat sensitive drugs and other necessary excipients. Polymer glass transition temperatures can also be further reduced to facilitate processing at lower temperature with optional addition of plasticisers.

Illustratively, WO 9614058 provides a sustained-release pharmaceutical formulation, comprising a melt-extruded blend of a therapeutically active agent, one or more materials selected from the group consisting of alkylcelluloses, acrylic and methacrylic acid polymers and copolymers, shellac, zein, hydrogenated castor oil, hydrogenated vegetable oil, and mixtures thereof; and one or more hydrophobic fusible carriers which provide a further retardant effect and are selected from the group consisting of natural or synthetic waxes, fatty acids, fatty alcohols, and mixtures thereof, the fusible carrier having a melting point from 30 to 200° C. The melt-extruded blend is divided into a unit dose containing an effective amount of said therapeutically active agent to render a desired therapeutic effect and providing a sustained-release of said therapeutically active agent for a time period of from about 8 to about 24 hours.

Furthermore, WO 9614058 describes a method of preparing a sustained-release pharmaceutical extrudate suitable for oral administration. The method comprises:

blending a therapeutically active agent together with (1) a material selected from the group consisting of alkylcelluloses, acrylic and methacrylic acid polymers and copolymers, shellac, zein, hydrogenated castor oil, hydrogenated vegetable oil, and mixtures thereof and (2) a fusible carrier selected from the group consisting of natural or synthetic waxes, fatty acids, fatty alcohols, and mixtures thereof; said retardant material having a melting point between 30-200° C. and being included in an amount sufficient to further slow the release of the therapeutically active agent, heating said blend to a temperature sufficient to soften the mixture sufficiently to extrude the same;

extruding said heated mixture as a strand having a diameter of from 0.1-3 mm;

cooling said strand; and dividing said strand to form non-spheroidal multi-particulates of said extrudate having a length from 0.1-5 mm; and dividing said non-spheroidal multi-particulates into unit doses containing an effective amount of said therapeutically active agent, said unit dose providing a sustained-release of said therapeutically active agent for a time period of from about 8 to about 24 hours.

In certain preferred embodiments of WO 9614058, the hydrophobic material is a pharmaceutically acceptable acrylic polymer, including but not limited to acrylic acid and methacrylic acid copolymers, methyl methacrylate, methylmethacrylate copolymers, ethoxyethyl methacrylates, cynaoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methacrylate copolymers. Thus, in many of the Examples, the hydrophobic material is Eudragit RS PO (poly(ethyl acrylate, methyl methacrylate, trimethylammonium methacrylate chloride)), optionally in the presence of Eudragit L100 (poly (methacrylic acid, methyl methacrylate)).

SUMMARY OF THE INVENTION

The present invention provides formulations which employ a neutral poly(ethyl acrylate, methyl methacrylate) copolymer as a pharmaceutically acceptable carrier. Such a copolymer can impart controlled release properties to the formulation. Furthermore, with the present invention, we are able to provide a rubbery formulation through the use of melt extrusion.

Neutral poly(ethyl acrylate, methyl methacrylate) copolymer is commercially available in the form of an aqueous dispersion. Two such products, Eudragit NE 30 D and Eudragit NE 40 D, comprise respectively 30% and 40% of the polymer. In particular, Eudragit NE 30 D forms water-insoluble films and is suitable for granulation processes in the manufacture of matrix tablets and sustained-release coatings without any plasticiser addition. Information on the use of Eudragit NE to prepare tablets and coatings can be obtained from the following website: http://www.roehm.de/en/pharmapolymers.html.

For example, the website has a technical article describing how to make ibuprofen sustained release matrix tablets, by wet granulation using Eudragit NE 30 D as a binder and diffusion controlling agent. Granules are made by mixing ibuprofen with the Eudragit dispersion, grinding through a sieve, and drying. The granules are ground, mixed with disintegrant and other ingredients, and then compressed to tablets. The amount of Eudragit NE is relatively low.

In WO 03004009, Eudragit NE is among a list of suggested hydrophobic components for use with hydrophilic erodible components and a poorly compressible pharmaceutical agent. Seemingly the intention was to refer to another Eudragit, since Eudragit NE is a wet dispersion, and an objective of WO 03004009 is to form a compressible formulation by a process other than wet granulation.

Sood et al. describe the use of extrusion-spheronization to develop controlled release dosage forms for diltiazem hydrochloride in Pharmaceutical Technology 2004 (April): 62-85. A series of candidate materials were evaluated as pellet matrix-forming agents in a process involving wet granulation, extrusion of the wet granules, and spheronisation to form wet pellets which were then dried. Eudragit NE 30 D was tested in formulations D19 and D20, and gave no improvement in controlling drug release.

In the present invention we can employ neutral poly(ethyl acrylate, methyl methacrylate) copolymer as a carrier in a formulation. Typically the formulation of this invention uses a neutral poly(ethyl acrylate, methyl methacrylate) copolymer to provide a matrix within which is dispersed an active ingredient. Thus, for example, the invention provides multiparticulates each with such a matrix.

The formulations of this invention can take the form of a unit dose such as a capsule with a fill of multiparticulates with neutral poly(ethyl acrylate, methyl methacrylate) copolymer as carrier. The multiparticulates can be extrudates formed by extrusion of a dry mix, notably a mixture of dry granulates, which includes a neutral poly(ethyl acrylate, methyl methacrylate) copolymer.

Especially by the use of extrusion, the present invention provides controlled release multiparticulates which take the form of a cylinder or are generally spherical, ellipsoidal or disc shaped.

To this end, the invention further provides a dry mix as unfinished composition comprising a neutral poly(ethyl acrylate, methyl methacrylate) copolymer and an active ingredient. Such a composition is substantially free of water and is suited for extrusion as part of a process to provide a formulation of this invention. Typically the unfinished composition is a dry granulate and can be an extruded granulate.

In particular, we provide a dry granulate of neutral poly (ethyl acrylate, methyl methacrylate) copolymer and an active ingredient, where the level of neutral poly(ethyl acrylate, methyl methacrylate) copolymer is relatively high in order to impart the desired properties. Typically, amounts of 20 to 66% by weight of neutral poly(ethyl acrylate, methyl methacrylate) copolymer in the dry granulate are employed.

According to the present invention, we also provide a process for preparing a controlled release pharmaceutical extrudate, wherein the mix for extrusion includes a neutral poly (ethyl acrylate, methyl methacrylate) copolymer.

Another aspect of this invention resides in a method of administration of an active ingredient, wherein the active ingredient is administered as a controlled release formulation employing a neutral poly(ethyl acrylate, methyl methacrylate) copolymer as pharmaceutically acceptable carrier.

A related aspect of this invention is the use of a neutral poly(ethyl acrylate, methyl methacrylate) copolymer in the preparation of a pharmaceutical formulation to provide resistance to tamper, which is of importance where the active ingredient is open to abuse. The invention provides a method of imparting tamper resistance to a pharmaceutical formulation which comprises the incorporation of a neutral poly (ethyl acrylate, methyl methacrylate) copolymer with the active ingredient in the formulation.

BRIEF DESCRIPTION OF THE DRAWINGS

Reference is made in the experimental section to the accompanying drawings, in which.

DISCUSSION OF PREFERRED EMBODIMENTS

Figure 1:
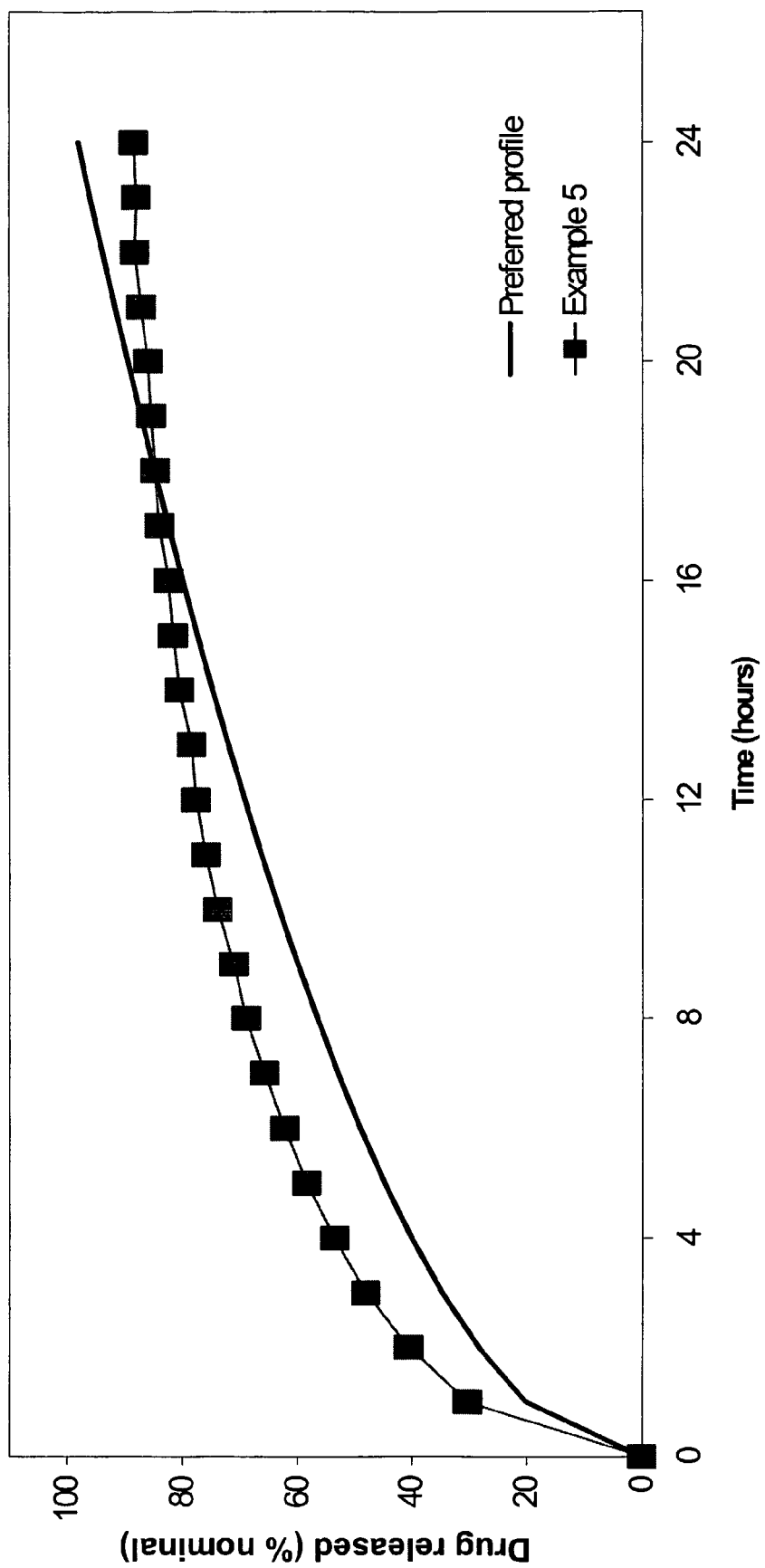
FIG. 1 shows the dissolution of oxycodone from pellets made in Example 5.

We find that by utilising a neutral poly(ethyl acrylate, methyl methacrylate) copolymer in the preparation of controlled release pharmaceutical extrudates, we can obtain melt extruded multiparticulates which exhibit rubber-like characteristics. Such rubbery extrudates can exhibit enhanced resistance to tamper. In particular, it appears that the rubbery characteristics are imparted by the step of melt extrusion.

In one aspect, the invention provides a controlled release pharmaceutical formulation obtained or obtainable by melt extrusion and including a neutral poly(ethyl acrylate, methyl methacrylate) copolymer and an active ingredient.

In a related aspect, the present invention provides a formulation which includes rubber-like multiparticulates.

The rubber-like characteristics provide multiparticulates which typically are elastic and compressible without breaking, and preferably resilient.

In one preferred form, as a demonstration of the rubber-like characteristics, the multiparticulates may be compressed by hand between two rigid surfaces, for example a coin and a table top or between two spoons, without breaking. The multiparticulates usually may be distorted but do not break or shatter and may ideally reassume more or less their original shape.

The rubbery characteristics can help impart resistance to tamper. Tamper resistance is of especial importance for products containing opioid analgesics or other active ingredients which are subject to abuse. The tamper resistance of preferred multiparticulates of the invention can be demonstrated by shaking a dosage amount of multiparticulates in water and/or ethanol, for example 40% ethanol.

For example a dosage amount of multiparticulates may be admixed with 10 ml of the liquid (water and/or ethanol) in a glass flask and then subjected to shaking at 500 to 600 oscillations per minute for 15 minutes using a Stuart Scientific Shaker, Model SF1, optionally after standing for 5 minutes. The amounts of active agent extracted can then be determined by HPLC and detection by UV for instance at 210 nm wavelength.

When tested in this way preferred multiparticulates in accordance with the invention showed at least one of the following release characteristics of active agent:

15 minutes shaking in water at room temperature: less than 10% release of active agent, preferably less than 7.5% release of active agent, more preferably less than 5% release of active agent, for example 1.5 to 4% release of active agent.

5 minutes standing in water at 50° C. followed by 15 minutes shaking at the same temperature: less than 20% release of active agent, preferably less than 15% release of active agent, more preferably less than 12% release of active agent, for example 4 to 12% release of active agent.

5 minutes standing at 75° C. followed by 15 minutes shaking at the same temperature: less than 25% release of active agent, preferably less than 20% release of active agent, more preferably less than 15% release of active agent, for example 10 to 15% release of active agent.

5 minutes standing at 100° C. followed by 15 minutes shaking at the same temperature: less than 30% release of active agent, preferably less than 25% release of active agent, more preferably less than 20% release of active agent, for example 12 to 20% release of active agent.

15 minutes shaking in 40% ethanol at room temperature: less than 35% release of active agent, preferably less than 30% release of active agent, more preferably less than 25% release of active agent, for example 15 to 25% release of active agent.

Alternatively, the tamper resistance of preferred multiparticulates of the invention can be demonstrated by subjecting a dosage amount of multiparticulates to grinding in a mortar and pestle with 24 rotations of the pestle and the product placed in 900 ml water at 37° C. for 45 minutes. The amounts of active agent extracted can then be determined by HPLC and detection by UV for instance at 210 nm wavelength.

When tested using this method, preferred multiparticulates according to the invention showed the following release characteristics of active agent; less than 12.5% release of active agent, preferably less than 10% release of active agent, more preferably less than 7.5% release of active agent, for example 2 to 7.5% release of active agent.

In a further method, the tamper resistance of preferred multiparticulates of the invention can be demonstrated by crushing a dosage amount of multiparticulates between two spoons or in a pill crusher, such as a Pill Pulverizer as sold by Apex Healthcare Products, and then extracting in 2 ml water heated to boiling on a spoon and filtered off. The amounts of active agent extracted can then be determined by HPLC and detection by UV for instance at 210 nm wavelength.

When tested using this method, preferred multiparticulates according to the invention showed the following release characteristics of active agent; less than 27.5% release of active agent, preferably less than 15% release of active agent, more preferably less than 5% release of active agent, for example 1 to 5% release of active agent.

For imparting such tamper resistance, the present invention provides the use of a neutral poly(ethyl acrylate, methyl methacrylate) copolymer in the preparation of a pharmaceutical formulation to provide resistance to tamper. A neutral poly(ethyl acrylate, methyl methacrylate) copolymer is incorporated with the active ingredient in the formulation.

In one aspect, the invention provides a method of imparting tamper resistance in a pharmaceutical formulation, which comprises admixing an active ingredient and a neutral poly (ethyl acrylate, methyl methacrylate) copolymer, and forming a pharmaceutical formulation incorporating the active ingredient with the neutral poly(ethyl acrylate, methyl methacrylate) copolymer.

The neutral poly(ethyl acrylate, methyl methacrylate) copolymer is suitably employed in an amount by weight of up to 66% in the mix for extrusion, say 20 to 66% of the extrusion mix, more typically from 20 to 50% of the extrusion mix, such as 30 to 40% of the extrusion mix. These percentages also apply to the amount of neutral poly(ethyl acrylate, methyl methacrylate) copolymer in a dry granulate of this invention.

The neutral poly(ethyl acrylate, methyl methacrylate) copolymer can be employed with other ingredients including a drug or other active ingredient. The reader is referred to WO 9614058, incorporated herein in full by specific reference. The neutral poly(ethyl acrylate, methyl methacrylate) copolymer can form all or more preferably part of the release controlling material employed in the extrusion method of that patent specification.

In this respect, our preferred compositions include at least one other polymer to modify release. In particular, it appears that the use of ethyl cellulose or like polymer can assist in imparting resistance to tamper, especially resistance to extraction by alcohol. An alkyl cellulose such as ethyl cellulose is preferably employed for example in an amount of 5 to 60% w/w of the formulation, preferably 10 to 50% w/w of the formulation, most preferably 20 to 45% w/w of the formulation. Other suitable polymers include water insoluble ammonium methacrylate copolymers. The insoluble ammonium methacrylate copolymers may be Eudragit RS PO and Eudragit RL PO, which are ammonio methacrylate copolymers. In particular the at least one other polymer is typically a sparingly water permeable thermoplastic polymer or a relatively highly water permeable thermoplastic polymer which can significantly modify release but is to be used in an amount which does not impair resilience or flexibility.

A plasticiser and/or a lubricant is preferred when using an extruder with a relatively low torque capability such as a Leistritz Micro 18 machine. With a larger extruder, such as a Leistritz Micro 27, similar formulations, without or with relatively low levels of plasticiser and/or lubricant, may be processed.

The plasticiser is normally chosen from water insoluble solids such as cetyl alcohol, stearyl alcohol and cetostearyl alcohol; water soluble solids such as sorbitol and sucrose and high molecular weight polyethylene glycol, water insoluble liquids such as dibutyl sebacate and tributyl citrate and water soluble liquids such as triethyl citrate, propylene glycol and low molecular weight polyethylene glycol. Tributyl citrate is a preferred plasticiser. Stearyl alcohol is also a preferred plasticiser. Another preferred plasticiser is a high molecular weight polyethylene glycol of MW 1000 to 20000, such as PEG 6000.

A lubricant can be included. The lubricant is normally a solid at room temperature, and is suitably chosen from stearic acid, glycerol dibehenate, magnesium stearate, calcium stearate, talc and silicone dioxide (fused silica). The presence of lubricant in the melt extrusion formulation improves blending, kneading and conveying and reduces cohesion and adhesion forces. Smooth extrusion at low to moderate temperatures improves batch to batch reproducibility and reduces the strain on both the product and equipment. Stearic acid, possibly in the form of a salt, is a preferred lubricant. Another preferred lubricant is glycerol dibehenate.

A drug is usually present as active agent in the formulations of the invention. The reader is referred to WO 9614058 for examples. Oxycodone is a typical drug for use in the products and processes of this invention. Other opioids are for example hydromorphone, hydrocodone, fentanyl and analogues thereof, buprenorphine, diamorphine, meperidine, propoxyphene and diphenoxylate. Other active agents which may be formulated in accordance with the invention include stimulants such as dextroamphetamine, amphetamine, methamphetamine, sibutamine, methylphenidate; barbiturates such as methobarbitol and pentobarbital; anti-depressants such as diazepam, bromazepam, chlordiazepoxide, oxazepam, malprazolam, triazolam and etazolam, flunitrazapam and methaqualone; and dissociative anaesthetics such as ketamine; and salts, acid addition salts, and esters thereof.

Preferred multiparticulates of this invention therefore can comprise a neutral poly(ethyl acrylate, methyl methacrylate) copolymer; an active ingredient; at least one other polymer to modify release which is usually an alkyl cellulose; optionally a plasticiser; and optionally a lubricant.

Suitable percentage amounts for the preferred ingredients are given in the following table, based on the total weight of the specified ingredients:

|  | typical range | preferred range | more preferred range | most preferred range |
|---|---|---|---|---|
| water-insoluble neutral poly(ethyl acrylate, methyl methacrylate) copolymer | 5 to 66 | 15 to 50 | 20 to 45 | 25 to 45 |
| active agent* | up to 60 | 5 to 55 | 5 to 50 | 10 to 45 |
| further polymer to modify release | 0 to 85 | 5 to 75 | 5 to 60 | 5 to 45 |
| plasticiser | 0 to 30 | 0 to 25 | 3 to 25 | 3 to 20 |
| lubricant | 0 to 25 | 0 to 25 | 0 to 20 | 0 to 15 |

*The amount of active agent can be 0% in placebo formulations for trials or development work.

A typical formulation may contain as well as for example up to 60% w/w of the active agent or placebo, 15 to 50% w/w of neutral poly(ethyl acrylate, methyl methacrylate) copolymer; 5 to 60% w/w, suitably 15 to 50% w/w, for example 15 to 25% or 25 to 45%, of an alkyl cellulose, preferably ethyl cellulose; and 0 to 25%, preferably 7.5 to 20%, of one or more plasticisers, for example stearyl alcohol and tributyl citrate. For example up to 50% oxycodone can be present as active agent. These ingredients may be the only components, or if desired the formulations may contain additional components such as 5 to 60% of an insoluble ammonium methacrylate copolymer. Illustratively, the formulation can contain 10 to 60%, preferably 35 to 50% of an insoluble ammonium methacrylate copolymer which is of low permeability, such as Eudragit RS PO, and/or it can contain 5 to 40%, for example 5 to 30%, preferably for example 5 to 25%, of an ammonium methacrylate copolymer which is highly permeable, such as Eudragit RL PO.

Other additives may also be employed to produce multiparticulates within a set of predetermined specifications. Bulking agents for example lactose, microcrystalline cellulose and calcium phosphate, are widely used pharmaceutical excipients and can be used in the present invention to modify the release rates and/or total release. Other release modifying agents may also be considered to modulate the release rate and/or enhance total release.

The multiparticulates are preferably produced by melt extrusion of a granulate, and in particular by a process comprising wet granulation of the ingredients and drying of the granulates, and melt extrusion of the granulate.

The granulation step may be carried out using conventional procedures, for example using a high shear mixer such as a Gral mixer or a fluid bed granulator or a fluid bed granulator with a rotary insert.

When using a high shear mixer the process may comprise the following steps;
a) granulation, preferably wet granulation;
b) optionally extrusion of the granulate;
c) drying of the granulate or the extruded granulate, preferably by means of a fluid bed dryer;
d) optionally screening and/or milling the dried granulate or the dried extruded granulate from step c); and
e) melt extrusion of the product from step c) or d).

When using a fluid bed granulator with or without a rotary insert the process may comprise the following steps:
a) granulation;
b) optionally extrusion of the granulate;
c) drying of the granulate or the extruded granulate, preferably by means of a fluid bed dryer;
d) optionally screening and/or milling the product from step c); and
e) melt extrusion of the dried granulate or screened or milled product from step c) or step d).

The product from step (c) or (d) which is to be loaded into the melt extruder, that is the optionally milled or screened dried granulate, is itself a novel product of this invention.

The granulation step may be carried out using conventional procedures, for example using a high shear mixer such as a Gral. Typically the dry ingredients are added first; these are mixed by operation of the high shear mixer and then the dispersion of polymer is added by spraying or dropwise, and mixing continued.

Alternatively, for example, a liquid plasticiser may be added to the dry ingredients and mixed by operation of the high shear mixer and the dispersion of polymer is then added by spraying or dropwise and mixing continued.

The granulate may then be extruded in optional step (b), for example using an Alexanderwerk extruder. The extrudate is then dried using preferably a fluid bed dryer. The extrudate may be produced directly of a suitable size for fluid bed drying using a suitable extruder such as the aforementioned Alexanderwerk where the small blade breaks up the pellets, or may be broken down to a suitable size. Alternatively the granules produced by high shear mixing may be of a suitable size or broken down to a suitable size for drying followed by melt extrusion.

The dried material will typically contain less than 5% w/w water for example 2 to 3% w/w water, or less, such as trace amounts.

The melt extrusion process may be carried out in a manner similar to that described in WO 9614058.

For the present invention, we prefer to employ a twin screw extruder. Essentially, the dried granulate or milled product is fed by a feeder into the first segment of an extruder barrel preferably at relatively low temperature (for example 10-20° C.) to ensure a constant flow of material to the high temperature barrels. The feeder provides a uniform current of the material to the extruder. Consistency is desirable as irregular and variable feeding rates can produce multiparticulates with various physical properties, such as density and porosity.

The preferred extruder is designed with twin screws, which may have co-rotating or counter-rotating screws, for the tasks of conveying, blending and compressing the blend as well as providing mechanical energy. The extruder will be equipped with heating means and cooling means as required. The screws which perform a significant part of this melt extrusion process are built of different smaller elements. The mixing and kneading process can be significantly altered by changing the type, length and configuration of the screws elements. Short residence times and moderate to low shear forces contribute to safe processing and stable product even with heat sensitive drugs.

Screw rotating speeds may play a part in the quality of the multiparticulates produced. High rotation speeds without appropriate compensation of the feed rate may produce high porosity multiparticulates with a variable drug release rate. On the other hand slow screw rotation would induce unnecessary long residence times. A vacuum connected to the extruder barrel is desirable to remove trapped air and residual moisture from within the plastified material and thus produce dense multiparticulates ideally of low porosity.

The extrusion head is typically designed to produce multiple strands of fixed diameter, for example 1.0 mm. The number, shape and diameter of the orifices can be changed to suit a predetermined specification.

In addition to the screw speed, the other main influential parameters are the screw torque, individual barrel temperature, and extrusion head pressure and temperature.

In accordance with one cutting procedure of this invention, the extruded strands are carried away from the die-head on a conveyer. Strand diameter is affected by the starting material feed rate, the screws speed, barrel temperature, die-head orifice diameter and conveying speed and nip rolls speed. Conveying is appropriate to carry the extruded strands to a laser gauge or other measuring device. During this conveying process the strands cool down gradually, but essentially remain flexible. Flexible strands retain integrity on the laser gauging device, between the pelletiser feed nip rolls and during entry to the pelletiser. Rapidly cooled strands, depending on the formulation, may lose their integrity and shatter during passage through the nip rolls and pelletiser into uneven-shaped and irregular-sized multiparticulates.

A laser gauge may be used to provide a continuous measurement of strand diameter, for example 1.0 mm.

The measured strands are fed into the pelletiser by nip rollers. The pelletiser cuts the fed strands, for instance using a rotary knife cutter, to a pre-determined length, for example 1.0 mm. The feeding rate of the strands and the pelletiser cutter speed determine the length of the multiparticulates.

Overall, the co-ordination/interaction between the feeder, extruder, conveyor, and pelletiser is an important parameter affecting the quantity, quality and reproducibility of the final multiparticulate products.

Multiparticulates produced by this cutting procedure where the extruded strands are carried away from the die-head typically take the form of cylinders. Preferably the cylinders have a diameter of about 1 mm and a length of about 1 mm.

In another preferred cutting procedure, a cutter cuts the extruded mix as it emerges under pressure and still molten from the orifices of the die-plate. The cutter is suitably a rotary cutter with one or more blades which sweep over the surface of the die-head to pass the orifices. Two diametrically opposed blades are preferred. Ideally, the outer surface of the die-head is coated with a non-stick material, for example polytetrafluoroethylene (PTFE). As the cut extrudate multiparticulates expand and cool, they tend to form rounded surfaces. By appropriate adjustment of the rate of extrusion and the speed of the cutter blade, as well as generally cylindrical multiparticulates, it is possible for example to arrange for spherical or substantially spherical, ellipsoidal or disc shaped multiparticulates to be obtained. In one embodiment a stream of air is directed into the region of the surface of the die-head, the air being at a reduced temperature to cool the extrudate and to speed solidification.

Spherical multiparticulates produced by this method offer a number of advantages:

Better batch to batch reproducibility.
Easier coating and lower coating weight required.
Better capsule filling and higher yield.
More stable at elevated temperature.
More tamper resistant.
Reduce or eliminate some problems that arise during conveying and pelletising the strands such as strands fracturing to different length pellets and possible static charge.

The multiparticulates may be divided into unit doses such that each individual unit dose includes a dose of drug for administration to a mammal, preferably a human patient. For the preferred drug, oxycodone or a salt thereof, preferably the hydrochloride, a suitable dose of the active agent is 5 to 400 mg, especially 5 mg, 10 mg, 20 mg, 30 mg, 40 mg, 60 mg, 80 mg, 120 mg or 160 mg unit dosages. In this respect, a unit dose contains an effective amount of the therapeutically active agent to produce pain relief and/or analgesia to the patient. The dose of oxycodone administered to a patient will vary due to numerous factors, including the weight of the patient, tolerance, the severity of the pain, the metabolic status and the nature of any other therapeutic agents being administered.

The resultant multiparticulates can be employed as a fill in a capsule. Thus, the present invention provides a capsule suited for once or twice a day dosing. Other dosage forms of the controlled release formulation can be provided.

In one preferred embodiment, the multiparticulates are filled into gelatin capsules each containing a unit dose. The fill weight in the capsule is preferably in the range 80 to 500 mg, more preferably 120 to 500 mg. In a variation of this invention, the unit doses of multiparticulates may be incorporated into other solid pharmaceutical dosage formulations, for example using compression or shaping or forming into tablets, or by forming the extruded product into the form of a suppository.

The preferred capsules or other unit dose forms of this invention preferably are designed for administration at intervals of about 12 hours or 24 hours.

A preferred drug for inclusion in the multiparticulates is oxycodone or salt thereof, preferably the hydrochloride. A unit dose form suitable for 12-hourly dosing then suitably has an oxycodone dissolution rate in vitro, when measured by the USP Paddle Method (see the U.S. Pharmacopoeia XXII 1990) at 100 rpm in 900 ml aqueous buffer (pH between 1.6 and 7.2) at 37° C. of between 12.5 and 42.5% (by wt) oxycodone released after 1 hour, between 25 and 56% (by wt) oxycodone released after 2 hours, between 45 and 75% (by wt) oxycodone released after 4 hours and between 55 and 85% (by wt) oxycodone released after 6 hours.

A unit dose form containing oxycodone or a salt thereof, preferably the hydrochloride, suitable for 12 hourly dosing may also, suitably have the following dissolution rate in vitro when measured using the USP Basket Method <<7 11>> Apparatus 1 at 100 rpm in 900 ml aqueous buffer at pH 1.2 (simulated gastric fluid without enzyme) at 37° C. with detection by HPLC with UV at 206 nm wavelength; from 0 to 40%, preferably 25 to 35% at 1 hour; from 20 to 70%, preferably 40 to 60%, at 2 hours; from 40 to 80%, preferably 55 to 75%, at 3 hours; from 60 to 95%, preferably 65 to 90%, at 4 hours; and greater than 70% at 5 hours.

Furthermore, we prefer that the peak plasma level of oxycodone obtained in vivo occurs between 2 and 4.5 hours after administration of the dosage form.

More information on desirable characteristics for such oxycodone formulations is given in WO 9310765 which is incorporated herein in full by specific reference.

As an alternative, the oxycodone capsules or other unit dose forms of this invention are designed for administration at intervals of about 24 hours. To this end, the unit dose form suitably has an oxycodone dissolution rate in vitro, when measured by the USP Basket Method at 100 rpm in 900 ml aqueous buffer at a pH between 1.6 and 7.2 at 37° C. of from 0% to about 40% at 1 hour, from about 8% to about 70% at 4 hours, from about 20% to about 80% at 8 hours, from about 30% to about 95% at 12 hours, from about 35% to about 95% at 18 hours, and greater than about 50% at 24 hours.

Furthermore, we prefer that the peak plasma level of oxycodone obtained in vivo is reached at about 2 hours to about 17 hours after administration at steady state of the dosage form.

A unit dose form containing oxycodone or a salt thereof, preferably the hydrochloride, suitable for dosing every 24 hours, may also suitably have the following dissolution rate in vitro when measured using the USP Basket Method <<7 11>> Apparatus 1 at 100 rpm in 900 ml aqueous buffer at pH 1.2 (simulated gastric fluid without enzyme) at 37° C. with detection by HPLC with UV at 206 nm wavelength; from 10 to 30%, preferably 17 to 23%, at 1 hour; from 20 to 35%, preferably 24 to 32%, at 2 hours; from 35 to 75%, preferably 48 to 66%, at 8 hours; and greater than 50%, preferably 68 to 92%, at 16 hours.

More information on desirable characteristics for such oxycodone formulations is given in WO 02087512 which is incorporated herein in full by specific reference.

In a variation, the present invention provides unit doses which contain an opioid and an opioid antagonist effective to prevent tampering. In this respect, reference is made to WO 0313433 which is incorporated herein in full by specific reference. In particular, the unit dose can contain oxycodone and naltrexone.

To this end, the present invention provides melt extruded multiparticulates of an opioid such as oxycodone, and melt extruded multiparticulates of an opioid antagonist such as naltrexone. In a preferred formulation antagonist multiparticulates do not release the antagonist on conventional administration, and for example have a non-release coating. Both populations of opioid and opioid antagonist are preferably visually and physically identical.

An important aspect of this invention is a capsule with a unit dose fill of less than 500 mg, comprising up to about 350 mg of oxycodone multiparticulates, and up to about 200 mg of tamper-proof oxycodone antagonist multiparticulates. For example, there can be 120 to 300 mg of oxycodone multiparticulates, and 125 to 175 mg of tamper-proof oxycodone antagonist multiparticulates.

EXAMPLES OF THE INVENTION

Examples 1, 2 and 3

Three batches (Examples) of multiparticulates were manufactured following a similar procedure:

Step 1. Initially, the following items were placed into a Gral 10 high shear mixer, pre-heated to 40° C., and dry blended at high speed for 2 minutes:
Oxycodone Hydrochloride
Eudragit RS PO
Stearyl Alcohol
Stearic Acid Step 2. The Eudragit NE 40 D dispersion was screened through a 350 micron mesh to eliminate aggregates and transferred into a suitably sized container.

Step 3. The screened Eudragit NE 40 D dispersion was sprayed at low atomising pressure on to the dry blended materials from step 1 in the mixing bowl, whilst maintaining mixing/chopping.

Step 4. The application of Eudragit NE 40 D was continued until granule formation occurred.

Step 5. The application of Eudragit NE 40 D was periodically halted to scrape the sides of the mixing bowl.

Step 6. After all the Eudragit NE 40 D had been applied, the granules were dried under the same temperature conditions and at reduced mixing/chopping speeds.

Step 7. The granules were then fed at a controlled rate to a Leistritz Micro 18 extruder equipped with a conveyor and pelletiser. The extruder had a 1.5 mm die-plate, and heated Stations as follows; Stations 3 to 8, 90° C. to 100° C.; Stations 9 and 10, 100° C. The feed rate was 2.0 to 2.6 kg/hr and the screw speed 100 to 141 rpm, with a torque/melt pressure of 50 to 60%/40 to 50 bar.

The extruded strands were carried away from the die-head on a conveyor and cut into cylindrical multiparticulates.

|  | Examples (% w/w) | | |
| --- | --- | --- | --- |
| Material | Example 1 | Example 2 | Example 3 |
| Lactose anhydrous | 10.0 | 10.0 | |
| Oxycodone hydrochloride | | | 10.0 |
| Eudragit RS PO | 40.0 | 32.0 | 32.0 |
| Stearyl alcohol | 10.0 | 10.0 | 10.0 |
| Stearic acid | 6.0 | 6.0 | 6.0 |
| Eudragit NE* | 34.0 | 42.0 | 42.0 |
| Total | 100 | 100 | 100 |

*As Eudragit NE 40 D (water removed by drying)

Example 4

For this example, the alternate cutting procedure was employed. Extrudate emerges from the twelve orifices of the die-head of a Leistritz Micro 18 extruder. A rotary cutter with two blades is used to cut the extruded mix as it emerges under pressure and still molten from the orifices of the die-plate. The blades sweep over the surface of the die-head to pass the orifices. As they expand and cool, the cut extrudate particles tend to form rounded surfaces.

The following formulation was employed to produce placebo product containing lactose as a pharmaceutical non-active ingredient.

| Material | Example 4 (% w/w) |
| --- | --- |
| Lactose anhydrous | 10.0 |
| Eudragit RS PO | 37.0 |
| Stearyl alcohol | 10.0 |
| Stearic acid | 6.0 |
| Eudragit NE 40 D | 37.0* |
| Total | 100 |

*Value stated as solids content

* Value stated as solids content

By appropriate adjustment of the extrusion parameters including temperature and rates of extrusion, spherical or substantially spherical multiparticulates may be obtained.

Examples 5 and 6

Two batches of multiparticulates were planned using tributyl citrate as plasticiser (circa 43% w/w drug load). The percentage contents, w/w, were as follows.

|  | Examples (% w/w) | |
| --- | --- | --- |
| Material | 5 | 6 |
| Oxycodone hydrochloride | 42.2 | 42.2 |
| Ethyl cellulose N10 | 14.7 | 19.6 |
| Eudragit NE 40 D* | 35.3 (S), [88.3 (D)] | 29.4 (S), [73.5 (D)] |
| Tributyl citrate | 5.9 | 6.9 |
| Glycerol dibehenate | 2.0 | 1.9 |
| Total | 100 | 100 |

(S) = solid weight
(D) = dispersion weight
*40% dispersion (% w/w), water lost by evaporation A procedure for preparing multiparticulates of Example 5 in the form of pellets is as follows:

Step 1. The tributyl citrate was slowly added to ethyl cellulose in a Gral 10 high shear mixer and blended.

Step 2. The oxycodone was added to the blend from Step 1 in the Gral 10 high shear mixer and blended for 5 minutes.

Step 3. The Eudragit NE 40 D dispersion was screened through a 350 micron mesh to eliminate aggregates and transferred into a suitably sized container. The screened Eudragit NE 40 D dispersion was then slowly added by aid of a peristaltic pump onto the blended materials from Step 2 in the Gral 10 mixing bowl, pre-warmed to 38° C., whilst maintaining mixing/chopping.

Step 4. The application of Eudragit NE 40 D was continued until granule formation occurred—all the Eudragit NE 40 D was added.

Step 5. The application of Eudragit NE 40 D was periodically halted to permit scraping of the sides of the mixing bowl.

Step 6. After all the Eudragit NE 40 D had been added, the wet granules were extruded through a conventional extruder and the dried in a fluid bed dryer at approximately 42° C.

Step 7. The dried granules were cooled to room temperature and collected.

Step 8. The granules were then fed at a controlled rate to a Leistritz Micro 18 extruder equipped with a 1.0 mm die-plate, a conveyor and pelletiser under the same conditions as in Example 1. The extruded strands were carried away from the die-head on a conveyer and cut into cylindrical multiparticulates.

The procedure for the preparation of the formulation of Example 6 was the same as for Example 5 except in the following respects:

No plasticiser (tributyl citrate) was added in Step 1. Instead Step 1 was excluded and Step 2 consisted of mixing the oxycodone hydrochloride and the ethyl cellulose in the Gral 10 high shear mixer.

The granules were sieved (1.5 mm mesh) and the oversized granules milled (1.0 mm mesh) and recombined with the other granules.

Lubricant (glycerol dibehenate) was added to the dried granules immediately before feeding to the extruder at the end of Step 7.

The extruder had a die-plate with 1.5 mm orifices.

An alternate cutting procedure can be considered. Extrudate emerges from the orifices of the die-head of a Leistritz extruder. A rotary cutter with two blades is used to cut the extruded mix as it emerges under pressure and still molten from the orifices of the die-plate. The blades sweep over the surface of the die-head to pass the orifices. As they expand and cool, the cut extrudate particles tend to form rounded surfaces.

Although in the above Examples a Leistritz Micro 18 extruder was used, a larger extruder, for example a Leistritz Micro 27, may be preferred to handle materials requiring a higher torque for processing.

Extruded pellets obtained in Example 5 were dissolution tested using the USP Basket Method <<711>> Apparatus 1 at 100 rpm in 900 ml aqueous buffer at pH 1.2 (simulated gastric fluid without enzyme) at 37° C. with detection by HPLC with UV at 206 nm wavelength and gave the following results which are plotted in the accompanying FIG. 1 along with a preferred profile for a once-a-day product.

| Time (Hours) | Example 5<br>% oxycodone released |
| --- | --- |
| 0 | 0 |
| 1 | 30 |
| 2 | 41 |
| 3 | 48 |
| 4 | 53 |
| 5 | 58 |
| 6 | 62 |
| 7 | 66 |
| 8 | 69 |
| 9 | 71 |
| 10 | 74 |
| 11 | 76 |
| 12 | 78 |
| 13 | 78 |
| 14 | 81 |
| 15 | 82 |
| 16 | 82 |
| 17 | 84 |
| 18 | 85 |
| 19 | 85 |
| 20 | 86 |
| 21 | 87 |
| 22 | 88 |
| 23 | 88 |
| 24 | 88 |

Examples 7, 8 and 9

Using the same procedure and extrusion conditions as for the previous Examples apart from temperatures ranging from 100 to 120° C., a screw speed of up to 240 rpm and die-plate dimensions of 1.5 mm diameter (Examples 7 and 8) and 1.0 mm (Example 9), the following formulations were processed to produce multiparticulates.

| | Examples (% w/w) | | |
| --- | --- | --- | --- |
| Material | Example 7 | Example 8 | Example 9 |
| Oxycodone HCl | 43 | 43 | 43 |
| Ethyl cellulose N10 | 19 | 19 | 18 |
| Eudragit NE 40 D* | 29 | 29 | 27 |
| Tributyl citrate | 6 | 6 | 6 |
| Stearyl alcohol | | 3 | |
| Glycerol dibehenate | 3 | | 6 |
| Total | 100 | 100 | 100 |

*Value stated is solids content only. Liquid dispersion weight is (value/40) × 100

Examples 10 to 13

Using procedures similar to those of the previous Examples multiparticulates were produced with the following formulations.

| | Examples (% w/w) | | | |
| --- | --- | --- | --- | --- |
| Material | Example 10 | Example 11 | Example 12 | Example 13 |
| Oxycodone HCl | 10.0 | 10.0 | 10.0 | 10.0 |
| Ethyl cellulose N10 | 41.8 | nil | 32.0 | nil |
| Eudragit RS PO | nil | 41.8 | nil | 22.0 |
| Eudragit RL PO | nil | nil | 10.0 | 20.0 |
| Stearyl alcohol | 14.0 | 14.0 | 14.0 | 14.0 |
| Eudragit NE 40 D* | 34.2 (S), [85.5 (D)] | 34.2 (S), [85.5 (D)] | 34.0 (S), [85.0 (D)] | 34.0 (S), [85.0 (D)] |
| Total | 100 | 100 | 100 | 100 |

Figure 2:
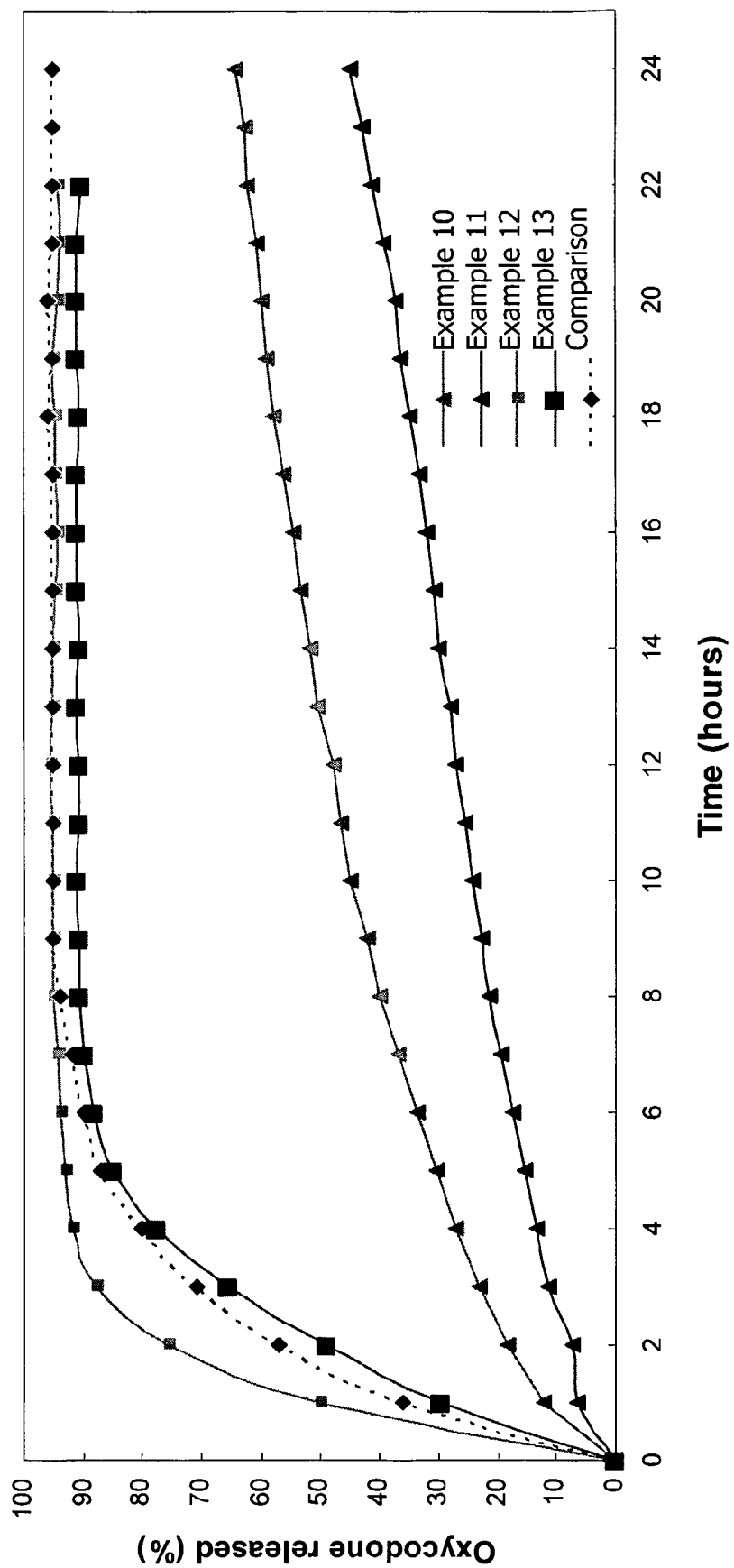
FIG. 2 shows the dissolution of oxycodone from pellets made in Examples 10 to 13.

(S) = solid weight
(D) = dispersion weight
*40% dispersion (% w/w), water lost by evaporation The above multiparticulates from Examples 10 to 13 were subjected to testing by dissolution using the USP Basket Method described above in Example 5. The results are shown in FIG. 2. These demonstrate that the release profiles of the multiparticulates of Examples 12 and 13 are similar in this test to the release profile of a preparation (Example 5 of our co-pending application publication number WO 2005/000310) which, when tested in vivo is substantially bioequivalent to OxyContin tablets.

The multiparticulates from Examples 10 and 11 have slower release profiles which may indicate they would be suitable for use in dosage forms for dosing at 24 hour intervals.

Figure 3:
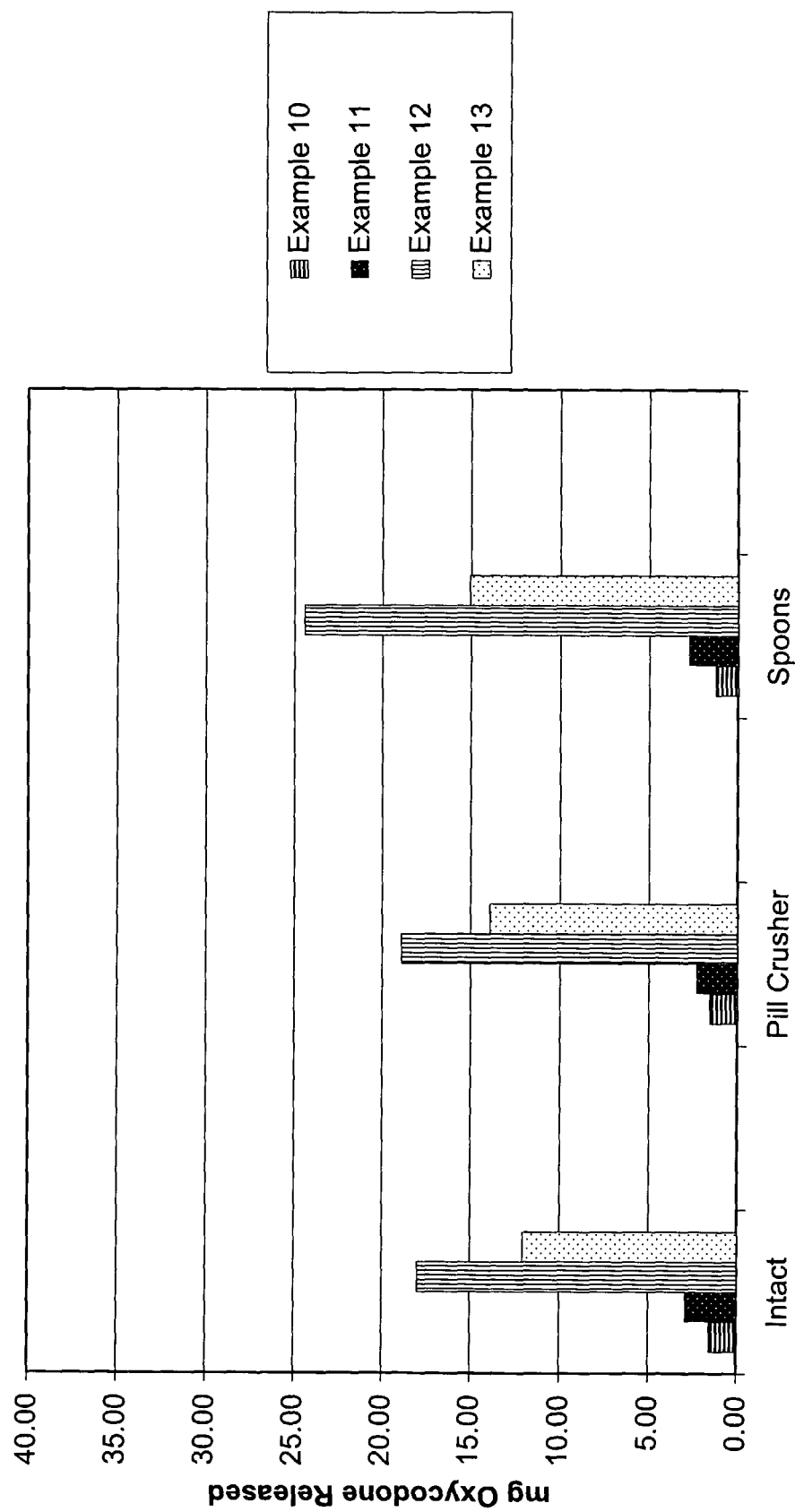
FIG. 3 shows dissolution of oxycodone from the crushed pellets of Examples 11 to 13.

The multiparticulates from Examples 10 to 13 were tested to determine their potential for tamper resistance as follows:

1) 400 mg of the multiparticulates from Examples 10 to 13 were either crushed between two spoons or in a pill crusher, such as a Pill Pulverizer as sold by Apex Healthcare Products, and then extracted in 2 ml water heated to boiling on a spoon and filtered off. The amounts of oxycodone extracted were then determined by HPLC and detection by UV at 210 nm wavelength and are shown in the chart of FIG. 3.

Figure 4:
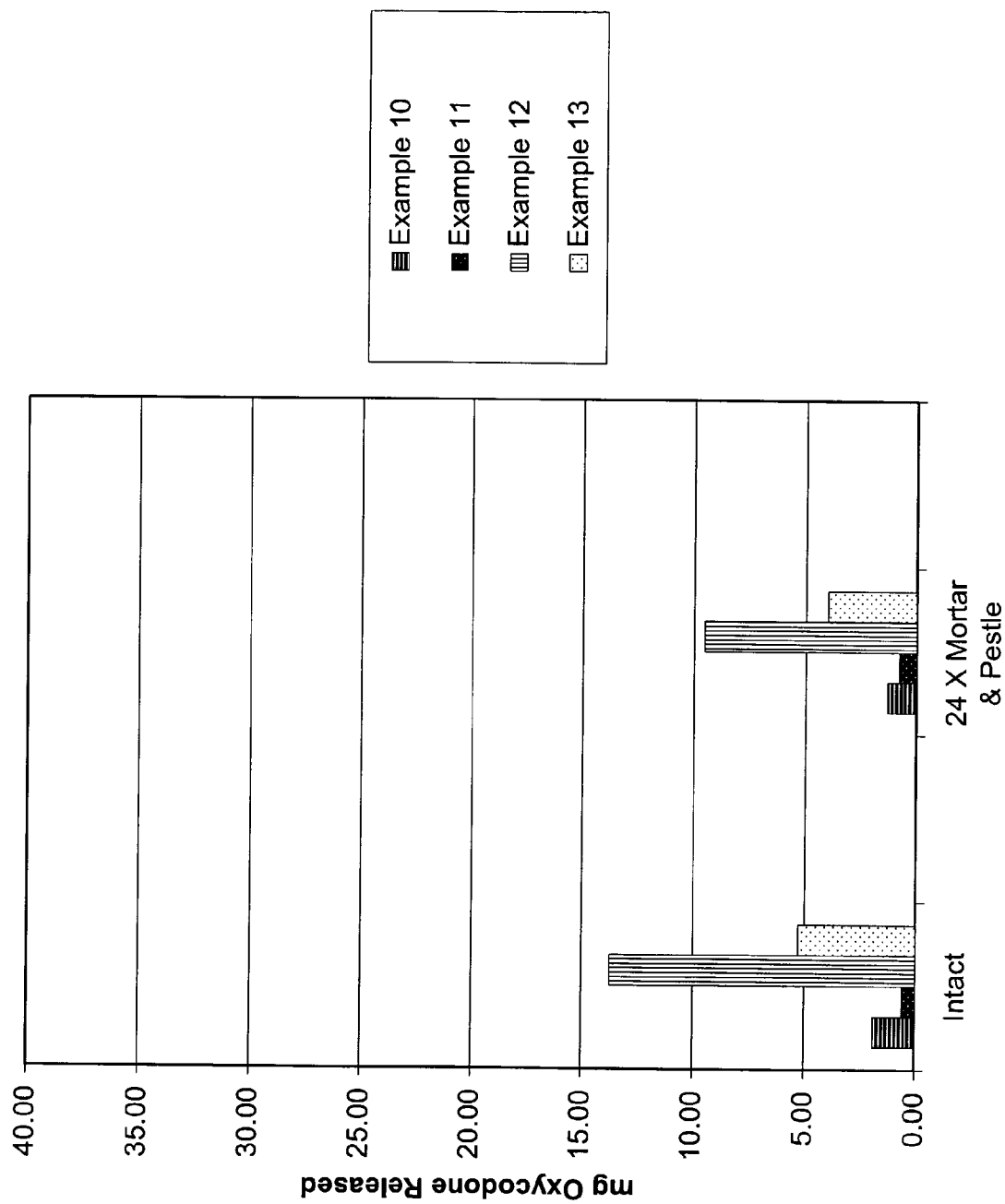
FIG. 4 shows the dissolution of oxycodone from the pellets of Examples 11 to 13 after milling using a pestle and mortar.

2) 400 mg of the multiparticulates from Examples 10 to 13 were subjected to grinding in a mortar and pestle with 24 rotations of the pestle and the product placed in 900 ml water at 37° C. for 45 minutes. The amount of oxycodone dissolved was then determined by the method described in 1) above and the results are represented in the bar chart of FIG. 4.

3) In each of extractions a) to e) 400 mg of the multiparticulates from one of Examples 10 to 13 were treated respectively as follows: the multiparticulates were placed in the solvent indicated in a glass flask which was then heated (if heating is indicated) over a water bath. The flask was then subjected to shaking for the time indicated using a Stuart Scientific Flask Shaker Model SF1 set at 500 to 600 oscillations per minute. After extraction the amount of oxycodone dissolved was then determined by the method used in 1).
  a) 15 minutes shaking in 10 ml water at room temperature;
  b) heating for 5 minutes in 10 ml water at 50° C. followed by 15 minutes shaking;
  c) heating for 5 minutes in 10 ml water at 75° C. followed by 15 minutes shaking;
  d) heating for 5 minutes in 10 ml water at 100° C. followed by 15 minutes shaking;
  e) 15 minutes shaking in 10 ml 40% ethanol at room temperature.

Figure 5:
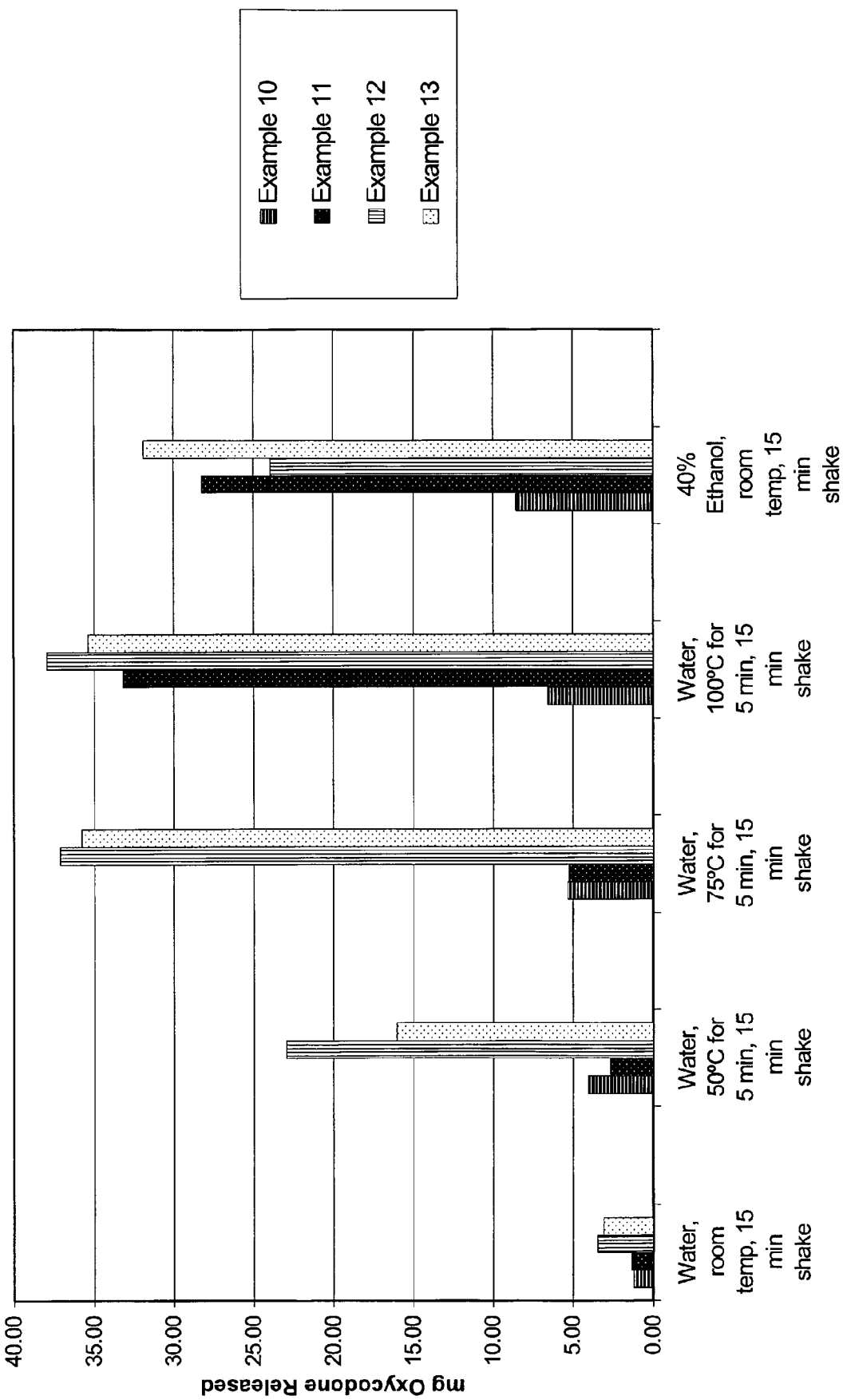
FIG. 5 shows the dissolution in solvents of oxycodone from the pellets of Examples 10 to 13.

The test results are shown in the attached bar chart of FIG. 5.

The invention claimed is:

1. A unit dose of a controlled release pharmaceutical formulation, wherein said formulation comprises a plurality of melt extruded multiparticulates comprising a rubbery matrix, wherein the multiparticulates are extrudates formed by melt extrusion of a dry mix including a neutral poly(ethyl acrylate, methyl methacrylate) copolymer and an active agent, and wherein the rubbery matrix includes the neutral poly(ethyl acrylate, methyl methacrylate) copolymer and the active agent.

2. The unit dose of claim 1, wherein said active agent is selected from the group consisting of an opioid, a stimulant, a barbiturate, an anti-depressant, a dissociative anaesthetic, and any two or more of the foregoing.

3. The unit dose of claim 2, wherein said active agent is oxycodone, or a pharmaceutically acceptable salt thereof.

4. The unit dose of claim 1, wherein said matrix includes at least one other polymer to modify release.

5. The unit dose of claim 4, wherein said other polymer is selected from the group consisting of an alkyl cellulose and a water insoluble ammonium methacrylate copolymer.

6. The unit dose of claim 5, wherein said other polymer is ethyl cellulose.

7. The unit dose of claim 6, wherein said amount of ethyl cellulose is 10 to 50% by weight of the formulation.

8. The unit dose of claim 1, which comprises the following amounts of ingredients, based on the total weight of the specified ingredients:

| | |
|---|---|
| water-insoluble neutral poly(ethyl acrylate, methyl methacrylate) copolymer | 15 to 50 |
| active agent | 5 to 55 |
| another polymer to modify release | 5 to 75 |
| a plasticiser | 0 to 25 |
| a lubricant | 0 to 25 |

9. The unit dose of claim 1, which comprises up to 60% w/w of said active agent, 15 to 50% w/w of neutral poly(ethyl acrylate, methyl methacrylate) copolymer; 5 to 60% w/w of ethyl cellulose; and 7.5 to 20% of plasticiser.

10. The unit dose of claim 9, which further contains 5 to 60% of an insoluble ammonium methacrylate copolymer.

11. The unit dose of claim 10, which contains 35 to 50% of an insoluble ammonium methacrylate copolymer which is of low permeability and/or 5 to 30% of an ammonium methacrylate copolymer which is highly permeable.

12. The unit dose of claim 1, which contains a bulking agent.

13. The unit dose of claim 1, which contains an opioid and an opioid antagonist.

14. The unit dose of claim 13, which comprises 120 to 300 mg of oxycodone multiparticulates and 125 to 175 mg of oxycodone antagonist multiparticulates.

15. The unit dose of claim 1, which contains oxycodone and naltrexone.

16. The unit dose of claim 1, which contains oxycodone in an amount selected from the group consisting of 5 mg, 10 mg, 20 mg, 30 mg, 40 mg, 60 mg, 80 mg, 120 mg and 160 mg of oxycodone.

17. The unit dose of claim 1, suited for once a day dosing.

18. The unit dose of claim 17, wherein the active ingredient is oxycodone, and which has an oxycodone dissolution rate in vitro, when measured by the USP Basket Method at 100 rpm in 900 ml aqueous buffer at a pH between 1.6 and 7.2 at 37° C. of from 0% to about 40% at 1 hour, from about 8% to about 70% at 4 hours, from about 20% to about 80% at 8 hours, from about 30% to about 95% at 12 hours, from about 35% to about 95% at 18 hours, and greater than about 50% at 24 hours.

19. The unit dose of claim 18, wherein the peak plasma level of oxycodone obtained in vivo occurs at 2 hours to 17 hours after administration of the unit dose.

20. The unit dose of claim 17, wherein the active ingredient is oxycodone, and which has an oxycodone dissolution rate in vitro, when measured using the USP Basket Method <<7 11>> Apparatus 1 at 100 rpm in 900 ml aqueous buffer at pH 1.2 (simulated gastric fluid without enzyme) at 37° C. with detection by HPLC with UV at 206 nm wavelength; of from 10 to 30% at 1 hour; from 20 to 35% at 2 hours; from 35 to 75%, at 8 hours; and greater than 50% at 16 hours.

21. The unit dose of claim 1, suited for twice a day dosing.

22. The unit dose of claim 21, wherein the active ingredient is oxycodone, and which has an oxycodone dissolution rate in vitro, when measured by the USP Paddle Method of the U.S. Pharmacopoeia XXII (1990) at 100 rpm in 900 ml aqueous buffer (pH between 1.6 and 7.2) at 37° C. of between 12.5 and 42.5% (by wt) oxycodone released after 1 hour, between 25 and 56% (by wt) oxycodone released after 2 hours, between 45 and 75% (by wt) oxycodone released after 4 hours and between 55 and 85% (by wt) oxycodone released after 6 hours.

23. The unit dose of claim 21, wherein the active ingredient is oxycodone, and which has an oxycodone dissolution rate in vitro, when measured using the USP Basket Method <<7 11>> Apparatus 1 at 100 rpm in 900 ml aqueous buffer at pH 1.2 (simulated gastric fluid without enzyme) at 37° C. with detection by HPLC with UV at 206 nm wavelength; of from 0 to 40% at 1 hour; from 20 to 70%, at 2 hours; from 40 to 80%, at 3 hours; from 60 to 95%, at 4 hours; and greater than 70% at 5 hours.

24. The unit dose of claim 23, wherein the peak plasma level of oxycodone obtained in vivo occurs between 2 and 4.5 hours after administration of the unit dose.

25. The unit dose of claim 1, which shows at least one of the following characteristics (a) to (e) when tested by a test method comprising admixing a dosage amount of multiparticulates with 10 ml of the liquid in a glass flask and shaking at 500 to 600 oscillations per minute for 15 minutes using a Stuart Scientific Shaker Model SF1:
  a. 15 minutes shaking in water at room temperature: less than 7.5% release of active agent;
  b. 5 minutes standing in water at 50° C. followed by 15 minutes shaking at the same temperature: less than 15% release of active agent;
  c. 5 minutes standing in water at 75° C. followed by 15 minutes shaking at the same temperature: less than 20% release of active agent;
  d. 5 minutes standing in water at 100° C. followed by 15 minutes shaking at the same temperature: less than 25% release of active agent;
  e. 15 minutes shaking in 40% ethanol at room temperature: less than 25% release of active agent.

26. A plurality of controlled release melt extruded multiparticulates comprising a rubbery matrix, wherein the multiparticulates are extrudates formed by melt extrusion of a dry mix including a neutral poly(ethyl acrylate, methyl methacrylate) copolymer and an active agent, and wherein the rubbery matrix includes the neutral poly(ethyl acrylate, methyl methacrylate) copolymer and the active agent.

27. The plurality of controlled release melt extruded multiparticulates of claim 26, wherein said active agent is selected from the group consisting of an opioid, a stimulant, a barbiturate, an anti-depressant, a dissociative anaesthetic, and any two or more of the foregoing.

28. The plurality of controlled release melt extruded multiparticulates of claim 27, wherein said active agent is oxycodone, or a pharmaceutically acceptable salt thereof.

29. The plurality of controlled release melt extruded multiparticulates of claim 26, wherein said matrix includes at least one other polymer to modify release.

30. The plurality of controlled release melt extruded multiparticulates of claim 29, wherein said other polymer is selected from the group consisting of an alkyl cellulose and a water insoluble ammonium methacrylate copolymer.

31. The plurality of controlled release melt extruded multiparticulates of claim 30, wherein said other polymer is ethyl cellulose.

32. The plurality of controlled release melt extruded multiparticulates of claim 31, wherein said amount of ethyl cellulose is 10 to 50 by weight of the multiparticulates.

33. The plurality of controlled release melt extruded multiparticulates of claim 26, which comprises the following amounts of ingredients, based on the total weight of the specified ingredients:

| | |
|---|---|
| water-insoluble neutral poly(ethyl acrylate, methyl methacrylate) copolymer | 15 to 50 |
| active agent | 5 to 55 |
| another polymer to modify release | 5 to 75 |
| a plasticiser | 0 to 25 |
| a lubricant | 0 to 25 |

34. The plurality of controlled release melt extruded multiparticulates of claim 26, which comprises up to 60% w/w of said active agent, 15 to 50% w/w of neutral poly(ethyl acrylate, methyl methacrylate) copolymer, 5 to 60% w/w of ethyl cellulose; and 7.5 to 20% of plasticiser.

35. The plurality of controlled release melt extruded multiparticulates of claim 34, which further contains 5 to 60% of an insoluble ammonium methacrylate copolymer.

36. The plurality of controlled release melt extruded multiparticulates of claim 35, which contains 35 to 50% of an insoluble ammonium methacrylate copolymer which is of low permeability and/or 5 to 30% of an ammonium methacrylate copolymer which is highly permeable.

37. The plurality of controlled release melt extruded multiparticulates of claim 26, which contains a bulking agent.

38. The plurality of controlled release melt extruded multiparticulates of claim 26, which contains an opioid and an opioid antagonist.

39. The plurality of controlled release melt extruded multiparticulates of claim 38, which comprises 120 to 300 mg of oxycodone multiparticulates and 125 to 175 mg of oxycodone antagonist multiparticulates.

40. The plurality of controlled release melt extruded multiparticulates of claim 26, which contains oxycodone and naltrexone.

41. The plurality of controlled release melt extruded multiparticulates of claim 26, which contains oxycodone in an amount selected from the group consisting of 5 mg, 10 mg, 20 mg, 30 mg, 40 mg, 60 mg, 80 mg, 120 mg and 160 mg of oxycodone.

42. The plurality of controlled release melt extruded multiparticulates of claim 26, suited for once a day dosing.

43. The plurality of controlled release melt extruded multiparticulates of claim 42, wherein the active ingredient is oxycodone, and which has an oxycodone dissolution rate in vitro, when measured by the USP Basket Method at 100 rpm in 900 ml aqueous buffer at a pH between 1.6 and 7.2 at 37° C. of from 0% to about 40% at 1 hour, from about 8% to about 70% at 4 hours, from about 20% to about 80% at 8 hours, from about 30% to about 95% at 12 hours, from about 35% to about 95% at 18 hours, and greater than about 50% at 24 hours.

44. The plurality of controlled release melt extruded multiparticulates of claim 43, wherein the peak plasma level of oxycodone obtained in vivo occurs at 2 hours to 17 hours after administration of the multiparticulates.

45. The plurality of controlled release melt extruded multiparticulates of claim 42, wherein the active ingredient is oxycodone, and which has an oxycodone dissolution rate in vitro, when measured using the USP Basket Method <<7 11>> Apparatus 1 at 100 rpm in 900 ml aqueous buffer at pH 1.2 (simulated gastric fluid without enzyme) at 37° C. with detection by HPLC with UV at 206 nm wavelength; of from 10 to 30% at 1 hour; from 20 to 35% at 2 hours; from 35 to 75%, at 8 hours; and greater than 50% at 16 hours.

46. The plurality of controlled release melt extruded multiparticulates of claim 26, suited for twice a day dosing.

47. The plurality of controlled release melt extruded multiparticulates of claim 46, wherein the active ingredient is oxycodone, and which has an oxycodone dissolution rate in vitro, when measured by the USP Paddle Method of the U.S. Pharmacopoeia XXII (1990) at 100 rpm in 900 ml aqueous buffer (pH between 1.6 and 7.2) at 37° C. of between 12.5 and 42.5% (by wt) oxycodone released after 1 hour, between 25 and 56% (by wt) oxycodone released after 2 hours, between 45 and 75% (by wt) oxycodone released after 4 hours and between 55 and 85% (by wt) oxycodone released after 6 hours.

48. The plurality of controlled release melt extruded multiparticulates of claim 46, wherein the active ingredient is oxycodone, and which has an oxycodone dissolution rate in vitro, when measured using the USP Basket Method <<7 11>> Apparatus 1 at 100 rpm in 900 ml aqueous buffer at pH 1.2 (simulated gastric fluid without enzyme) at 37° C. with detection by HPLC with UV at 206 nm wavelength; of from 0 to 40% at 1 hour; from 20 to 70%, at 2 hours; from 40 to 80%, at 3 hours; from 60 to 95%, at 4 hours; and greater than 70% at 5 hours.

49. The plurality of controlled release melt extruded multiparticulates of claim 48, wherein the peak plasma level of oxycodone obtained in vivo occurs between 2 and 4.5 hours after administration of the multiparticulates.

50. The plurality of controlled release melt extruded multiparticulates of claim 26, which shows at least one of the following characteristics (a) to (e) when tested by a test method comprising admixing a dosage amount of the multiparticulates with 10 ml of the liquid in a glass flask and shaking at 500 to 600 oscillations per minute for 15 minutes using a Stuart Scientific Shaker Model SF1:
   a. 15 minutes shaking in water at room temperature: less than 7.5% release of active agent;
   b. 5 minutes standing in water at 50° C. followed by 15 minutes shaking at the same temperature: less than 15% release of active agent;
   c. 5 minutes standing in water at 75° C. followed by 15 minutes shaking at the same temperature: less than 20% release of active agent;
   d. 5 minutes standing in water at 100° C. followed by 15 minutes shaking at the same temperature: less than 25% release of active agent;
   e. 15 minutes shaking in 40% ethanol at room temperature: less than 25% release of active agent.

51. The unit dose of claim 1, further comprising a plasticiser in an amount of 3% to 14%.

52. The unit dose of claim 51, wherein the plasticizer is present in an amount of 3% to 10%.

53. The unit dose of claim 51, wherein the plasticiser is stearyl alcohol.

54. The plurality of controlled release melt extruded multiparticulates of claim 26, further comprising a plasticiser in an amount of 3% to 14%.

55. The plurality of controlled release melt extruded multiparticulates of claim 54, wherein the plasticiser is present in an amount of 3% to 10%.

56. The plurality of controlled release melt extruded multiparticulates of claim 54, wherein the plasticiser is stearyl alcohol.

* * * * *